(12) United States Patent
Nakayama et al.

(10) Patent No.: US 9,659,369 B2
(45) Date of Patent: May 23, 2017

(54) RADIOLOGICAL IMAGE RADIOGRAPHING DISPLAY METHOD AND SYSTEM THEREOF

(71) Applicant: FUJIFILM Corporation, Tokyo (JP)

(72) Inventors: Hiroki Nakayama, Ashigarakami-gun (JP); Akira Hasegawa, San Jose, CA (US); Harlan Romsdahl, San Jose, CA (US)

(73) Assignee: FUJIFILM Corporation, Tokyo (JP)

( * ) Notice: Subject to any disclaimer, the term of this patent is extended or adjusted under 35 U.S.C. 154(b) by 773 days.

(21) Appl. No.: 13/725,394

(22) Filed: Dec. 21, 2012

(65) Prior Publication Data

US 2013/0108138 A1 May 2, 2013

Related U.S. Application Data

(63) Continuation of application No. PCT/JP2011/064371, filed on Jun. 23, 2011.

(30) Foreign Application Priority Data

Jun. 30, 2010 (JP) ................................ 2010-148633

(51) Int. Cl.
*A61B 5/05* (2006.01)
*G06T 7/00* (2017.01)
(Continued)

(52) U.S. Cl.
CPC ............ *G06T 7/0014* (2013.01); *A61B 6/022* (2013.01); *A61B 6/502* (2013.01); *A61B 10/0233* (2013.01)

(58) Field of Classification Search
CPC ................................ A61B 6/022; A61B 6/502
(Continued)

(56) References Cited

U.S. PATENT DOCUMENTS 6,216,029 B1   4/2001  Paltieli
6,459,925 B1 * 10/2002 Nields ................. A61B 6/0435
                                                         128/915
(Continued)

FOREIGN PATENT DOCUMENTS

JP       63-244992 A    10/1988
JP     2000-500031 A     1/2000
(Continued)

OTHER PUBLICATIONS

International Search Report for PCT/JP/2011/064371 dated Jul. 19, 2011.
(Continued)

*Primary Examiner* — Rajeev Siripurapu
(74) *Attorney, Agent, or Firm* — Birch, Stewart, Kolasch & Birch, LLP

(57) ABSTRACT

Targeting of a lesion which is performed by a stereoscopic biopsy device or the like is performed simply and highly accurately. Designation of a predetermined position in the stereoscopic image is received to acquire position information when a stereoscopic image is displayed, radiological images of radiographing directions are displayed as two-dimensional images, a mark based on the position information, which is designated in the stereoscopic image, is displayed in the two-dimensional images, designation of a predetermined position in the two-dimensional images is further received to acquire the position information after the mark is displayed.

16 Claims, 10 Drawing Sheets

(51) Int. Cl.
*A61B 6/02* (2006.01)
*A61B 6/00* (2006.01)
*A61B 10/02* (2006.01)

(58) Field of Classification Search
USPC .......................................................... 600/427
See application file for complete search history.

(56) References Cited

U.S. PATENT DOCUMENTS

| | | | | |
|---|---|---|---|---|
| 2002/0041702 | A1* | 4/2002 | Takeo | G06T 7/0012 382/132 |
| 2006/0100507 | A1* | 5/2006 | Mertelmeier | A61B 6/502 600/425 |
| 2008/0031411 | A1* | 2/2008 | Klingenbeck-Regn | A61B 6/022 378/41 |
| 2009/0147074 | A1* | 6/2009 | Getty | A61B 6/466 348/51 |
| 2009/0238334 | A1* | 9/2009 | Brahme | A61B 6/022 378/41 |
| 2009/0257551 | A1* | 10/2009 | Dafni | A61B 6/022 378/6 |

FOREIGN PATENT DOCUMENTS

| | | |
|---|---|---|
| JP | 2000-107173 A | 4/2000 |
| JP | 2004-105746 A | 4/2004 |
| JP | 2007-130287 A | 5/2007 |
| JP | 2010-194194 A | 9/2010 |

OTHER PUBLICATIONS

Chinese Office Action, dated Oct. 29, 2014, for Chinese Application No. 201180029454.6, including an English translation thereof.
Japanese Office Action dated Mar. 4, 2014, issued in corresponding Japanese Patent Application No. 2010-148633.

* cited by examiner

RADIOLOGICAL IMAGE RADIOGRAPHING DISPLAY METHOD AND SYSTEM THEREOF

This application is a Continuation of PCT International Application No. PCT/JP2011/064371 filed on Jun. 23, 2011, which claims priority under 35 U.S.C 119(a) to Application No. 2010-148633 filed in Japan on Jun. 30, 2010, all of which are hereby expressly incorporated by reference into the present application.

BACKGROUND OF THE INVENTION

1. Field of the Invention

The present invention relates to radiological image radiographing and displaying method and system that displays a stereoscopic image using radiological images detected by a radiological image detector through irradiation of a subject with radiation from different directions, and more particularly, to use in a stereoscopic biopsy device that specifies a position of a lesion or the like in a stereoscopic image and collects a tissue fragment at the position.

2. Description of the Related Art

Tissue fragments around a lesion are often collected in hospital examinations. Recently, biopsy of piercing a patient with a tissue-collecting needle having a cavity (hereinafter, referred to as biopsy needle) and collecting a tissue filled in the cavity of the needle has attracted attention as a method of collecting a tissue fragment without giving a large burden to the patient. A stereoscopic biopsy device has been suggested as a device used to perform such a biopsy.

Such a stereoscopic biopsy device is to irradiate a test subject with radiation from different directions, to acquire plural radiological images having parallax, and to display a stereoscopic image (stereo image) on the basis of the acquired radiological images. The three-dimensional position of a lesion can be specified while observing the stereoscopic image, and a tissue fragment can be collected from a desired position by controlling the tip of a biopsy needle to reach the specified position.

SUMMARY OF THE INVENTION

Here, in the above-mentioned stereoscopic biopsy device, when targeting a lesion location from which a tissue fragment is collected, two radiological images constituting a stereoscopic image are displayed as two-dimensional images, the targeting is performed in the two-dimensional images, and then a three-dimensional position coordinate of the lesion location is calculated on the basis of the targeted positional coordinates in the two-dimensional images.

However, by merely individually targeting positions in two two-dimensional images as described above, it is difficult to check whether the same lesion is targeted in the two two-dimensional images. Particularly, when plural calcified portions exist in a radiological image of a breast, it is difficult to accurately select a corresponding calcified portion using two radiological images. In addition, when calcified portions different in the lateral direction are selected, a biopsy needle may pierce an improper position. For these reasons, the stereoscopic biopsy device of the related art takes a time of about 30 minutes to 1 hour, thereby causing a decrease in diagnostic efficiency.

For example, JP2000-500031T suggests that a position is targeted in a stereoscopic image while observing the stereoscopic image displayed on a display, but it is difficult to perform high-accuracy targeting in a stereoscopic image.

The present invention has been made in view of the above-mentioned problems and an object of the present invention is to provide radiological image radiographing and displaying method and system that can simply and highly accurately perform targeting of a lesion which is performed by a stereoscopic biopsy device or the like.

According to an aspect of the present invention, there is provided a radiological image radiographing and displaying method of acquiring adiological images radiographed in each radiographing direction which is detected by a radiological image detector through irradiation of a subject with radiation from different radiographing directions and displaying a stereoscopic image using the acquired radiological images radiographed in each radiographing direction, the method including: receiving designation of a predetermined position in the stereoscopic image and acquiring position information when the stereoscopic image is displayed; displaying each radiological image radiographed in each radiographing direction as two-dimensional images and displaying a mark based on the position information, which is designated in the stereoscopic image, in the two-dimensional images; and further receiving designation of a predetermined position in the two-dimensional images and acquiring the position information after the mark is displayed.

According to another aspect of the present invention, there is provided a radiological image radiographing and displaying system having a radiation emitting unit that irradiates a subject with radiation from different radiographing directions, a radiological image detector that detects the radiation emitted from the radiation emitting unit and passing through the subject, and a display unit that acquires radiological images radiographed in each radiographing direction which is detected by the radiological image detector and that displays a stereoscopic image using the acquired radiological images of the radiographing directions, the system including: a position designation receiving unit that receives designation of a predetermined position in the stereoscopic image when the stereoscopic image is displayed on the display unit; and a position information acquiring unit that acquires position information received by the position designation receiving unit, wherein the display unit displays each radiological image radiographed in each radiographing direction as two-dimensional images and displays a mark based on the position information acquired by the position information acquiring unit in the two-dimensional images, and wherein the position designation receiving unit further receives designation of a predetermined position in the two-dimensional images after the mark is displayed in the two-dimensional images, and the position information acquiring unit further acquires the received position information.

In the radiological image radiographing and displaying system, the display unit may simultaneously display the stereoscopic image and the two-dimensional images.

The display unit may display an image representing a predetermined threshold range in the two-dimensional images on the basis of coordinates in the depth direction of the position designated in the stereoscopic image.

The predetermined threshold range may be set depending on a resolution in the depth direction determined on the basis of the distance between the focal point of radiation of the radiation emitting unit and the radiological image detector and a convergence angle formed by the radiographing directions.

The radiological images displayed as the two-dimensional images may be acquired through irradiation with radiation from radiographing directions which form a convergence angle larger than the convergence angle formed by the radiographing directions of the radiological images constituting the stereoscopic image used to receive the designation of a position by the position designation receiving unit.

The radiological image radiographing and displaying system may further include an abnormal shadow detecting unit that detects an abnormal shadow in the two-dimensional images.

The display unit may display a mark representing the position of the abnormal shadow detected by the abnormal shadow detecting unit in the two-dimensional images.

The radiological image radiographing and displaying system may further include: a needle supporting unit that supports a biopsy needle and that is movable; a needle position controller that controls a position of a tip of the biopsy needle by causing the needle supporting unit to move on the basis of a predetermined position designated in the stereoscopic image or a predetermined position designated in the two-dimensional images; and an abnormal shadow determining unit that determines whether the abnormal shadow detected by the abnormal shadow detecting unit exists in a needle insertion path of the biopsy needle estimated on the basis of a predetermined position designated in the stereoscopic image or a predetermined position designated in the two-dimensional images.

The radiological image radiographing and displaying system may further include a needle insertion path receiving unit that receives designation of at least one point in a desired needle insertion path of the biopsy needle, and the abnormal shadow determining unit may determine whether the abnormal shadow exists in the needle insertion path which is estimated on the basis of a predetermined position designated in the stereoscopic image or a predetermined position designated in the two-dimensional images and the point received by the needle insertion path receiving unit.

When the abnormal shadow determining unit determines that the abnormal shadow does not exist, the needle position controller may control the needle supporting unit so that the biopsy needle moves along the estimated needle insertion path of the biopsy needle.

In the radiological image radiographing and displaying method and system according to the present invention, designation of a predetermined position in a stereoscopic image is received to acquire position information when the stereoscopic image is displayed, radiological images of radiographing directions are displayed as two-dimensional images, a mark based on the position information, which is designated in the stereoscopic image, is displayed in the two-dimensional images, designation of a predetermined position in the two-dimensional images is further received to acquire the position information after the mark is displayed. Accordingly, by displaying the mark based on the position information designated in the stereoscopic image in the two-dimensional images, an observer can easily perform targeting a lesion in the two-dimensional images and can finely adjust the position in the two-dimensional images, thereby performing targeting with higher accuracy.

DESCRIPTION OF THE PREFERRED EMBODIMENTS

Figure 1:
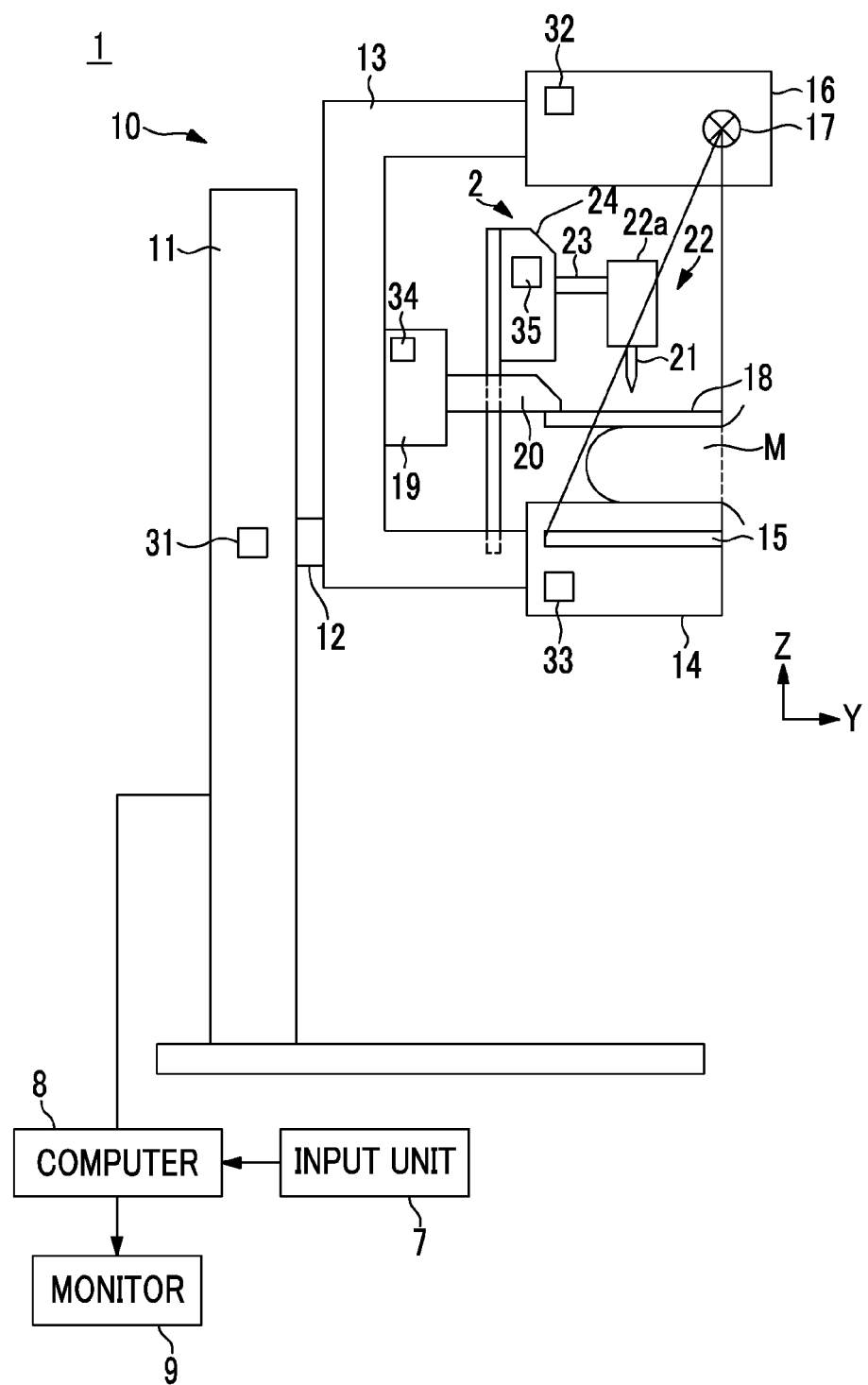
FIG. 1 is a diagram schematically illustrating the configuration of a stereoscopic breast image radiographing and displaying system employing an embodiment of a radiological image radiographing and displaying system according to the present invention.

Hereinafter, a stereoscopic breast image radiographing and displaying system employing an embodiment of a radiological image radiographing and displaying system according to the present invention will be described with reference to the accompanying drawings. The breast image radiographing and displaying system according to this embodiment is a system also serving as a breast stereoscopic biopsy device by having a detachable biopsy unit attached thereto. First, the schematic configuration of the entire breast image radiographing and displaying system according to this embodiment will be described. FIG. 1 is a diagram schematically illustrating the configuration of the breast image radiographing and displaying system having a biopsy unit attached thereto.

As shown in FIG. 1, the breast image radiographing and displaying system 1 according to this embodiment includes a breast image radiographing unit 10, a computer 8 connected to the breast image radiographing unit 10, and a monitor 9 and an input unit 7 connected to the computer 8.

Figure 2:
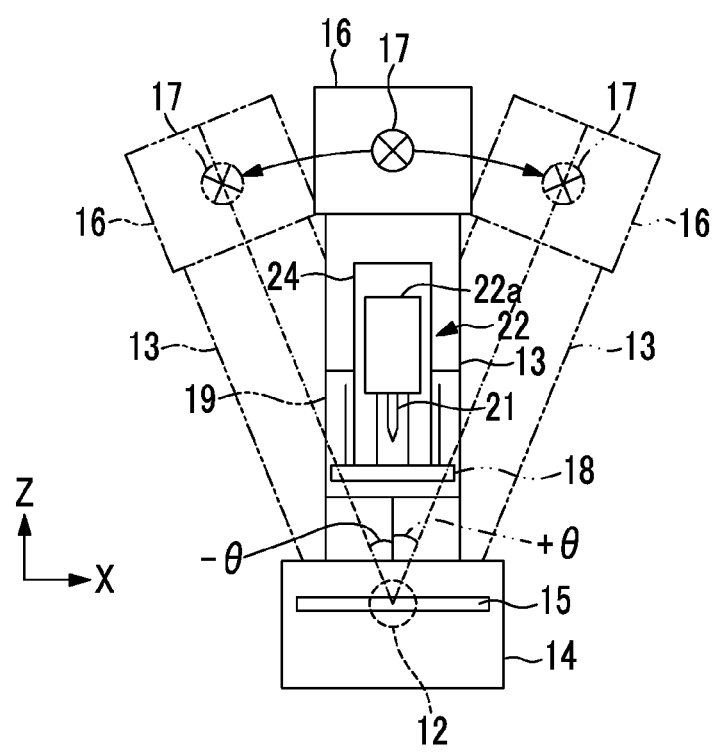
FIG. 2 is a diagram illustrating an arm unit of the stereoscopic breast image radiographing and displaying system shown in FIG. 1 when seen from the right side of FIG. 1.

As shown in FIG. 1, the breast image radiographing unit 10 includes a base 11, a rotation shaft 12 that can move vertically (in the Z direction) and rotate relative to the base 11, and an arm unit 13 connected to the base 11 via the rotation shaft 12. FIG. 2 shows the arm unit 13 when seen from the right side of FIG. 1.

The arm unit 13 has a letter C shape, a radiography platform 14 is mounted at one end thereof, and a radiation emitting unit 16 is mounted at the other end so as to oppose the radiography platform 14. The rotating and vertical moving directions of the arm unit 13 are controlled by an arm controller 31 assembled into the base 11.

A radiological image detector 15 such as a flat panel detector and a detector controller 33 controlling reading of charge signals from the radiological image detector 15 are built in the radiography platform 14. A circuit board including a charge amplifier converting the charge signals read from the radiological image detector 15 into voltage signals, a correlated double sampling circuit sampling the voltage signals output from the charge amplifier, and an AD converter converting the voltage signals into digital signals are built in the radiography platform 14.

The radiography platform 14 is configured to be rotatable about the arm unit 13. The direction of the radiography platform 14 can be set to a direction fixed relative to the base 11 even when the arm unit 13 rotates relative to the base 11.

The radiological image detector 15 can repeatedly record and read radiological images, and may employ a so-called direct radiological image detector that directly irradiates with radiation to generate charges or a so-called indirect radiological image detector that converts radiation into visible rays and converts the visible rays into charge signals. A so-called TFT reading method of reading radiological image signals by turning on and off a TFT (Thin Film Transistor) switch or a light reading method of reading radiological image signals by applying a reading beam can be preferably used as a method of reading radiological image signals. The method of reading radiological image signals is not limited to these methods, but other methods may be employed.

A radiation source 17 and a source controller 32 are received in the radiation emitting unit 16. The source controller 32 controls the time of emitting radiation from the radiation source 17 and radiation generating conditions (such as tube current, time, and tube current-time product) in the radiation source 17.

Figure 3:
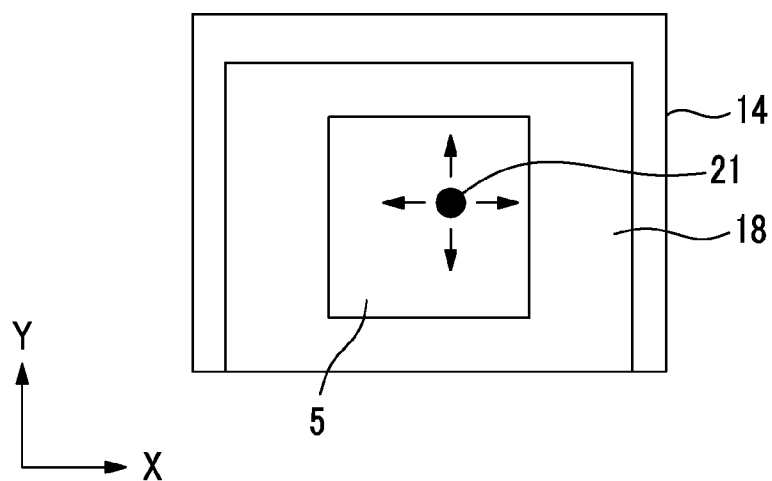
FIG. 3 is a diagram illustrating a radiography platform of the stereoscopic breast image radiographing and displaying system shown in FIG. 1 when seen from the upper side.

A compression plate 18 that is disposed above the radiography platform 14 so as to compress a breast, a support 20 that supports the compression plate 18, and a moving mechanism 19 that causes the support 20 to move in a vertical direction (the Z direction in FIG. 1) are disposed at the center of the arm unit 13. The position and the compressing pressure of the compression plate 18 is controlled by a compression plate controller 34. FIG. 3 is a diagram illustrating the compression plate 18 shown in FIG. 1 when seen from the upper side. As shown in the drawing, the compression plate 18 includes an opening 5 with a size of about 10×10 cm so as to perform biopsy in a state where a breast is fixed by the radiography platform 14 and the compression plate 18.

The biopsy unit 2 is mechanically and electrically connected to the breast image radiographing and displaying system 1, by inserting the base part thereof into the opening of the support 20 of the compression plate 18 and attaching the lower end of the base part to the arm unit 13.

The biopsy unit 2 includes a biopsy needle unit 22 having a biopsy needle 21 piercing a breast and being attachable and detachable, a needle support 23 supporting the biopsy needle unit 22, and a moving mechanism 24 causing the biopsy needle unit 22 to move in the X, Y, and Z directions shown in FIGS. 1 to 3 by causing the needle support 23 to move along a rail or causing the needle support 23 to retract or protrude. The position of the tip of the biopsy needle 21 of the biopsy needle unit 22 is recognized and controlled as a position coordinate (x, y, z) in a three-dimensional space by a needle position controller 35 included in the moving mechanism 24. The paper-perpendicular direction in FIG. 1 is defined as an X direction, the paper-perpendicular direction in FIG. 2 is defined as a Y direction, and the paper-perpendicular direction in FIG. 3 is defined as a Z direction.

Figure 4:
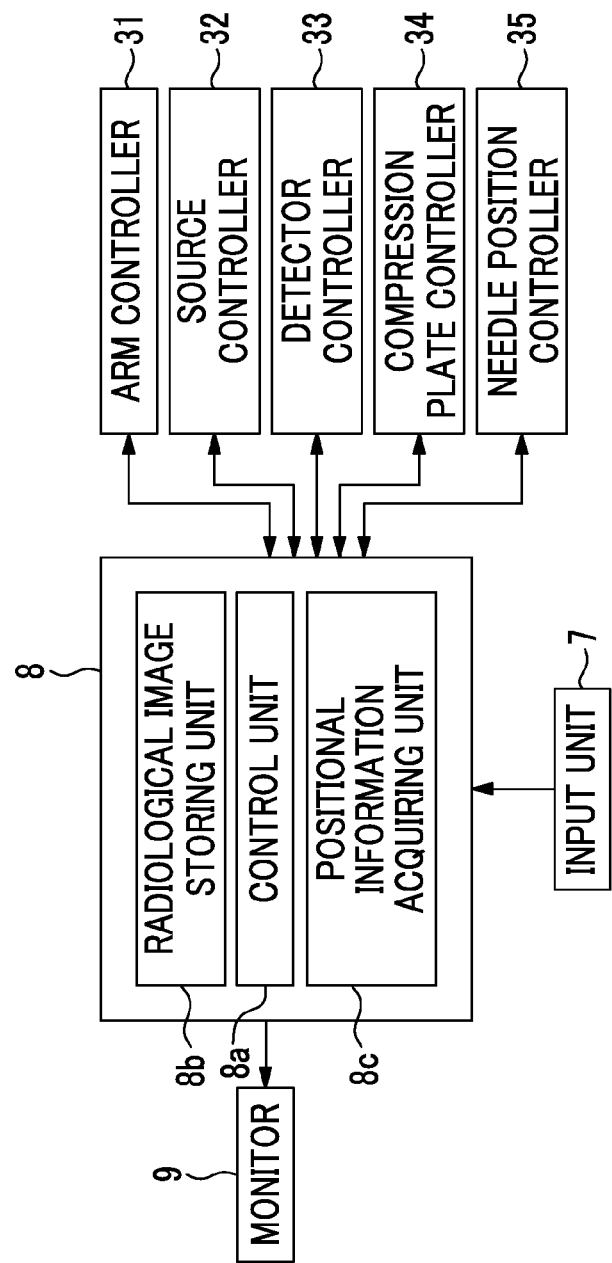
FIG. 4 is a block diagram schematically illustrating the internal configuration of a computer of the stereoscopic breast image radiographing and displaying system shown in FIG. 1.

The computer 8 includes a central processing unit (CPU) and a storage device such as a semiconductor memory, a hard disk, or an SSD, and a control unit 8a, a radiological image storage unit 8b, and a position information acquiring unit 8c shown in FIG. 4 are constructed by these hardware constituents.

The control unit 8a serves to output predetermined control signals to various controllers 31 to 35 and to control the entire system. The specific control method will be described later in detail.

The radiological image storage unit 8b stores in advance a radiological image signal for each radiographing direction acquired by the radiological image detector 15.

The position information acquiring unit 8c acquires position information such as abnormal shadow designated in a stereoscopic image and radiological images, displayed as two-dimensional images which are radiological images constituting the stereoscopic image, which are displayed on the monitor 9, and outputs the acquired position information to the control unit 8a.

The input unit 7 includes a pointing device such as a keyboard or a mouse and is configured to designate a position of abnormal shadow or the like in the stereoscopic image displayed on the monitor 9 and in the radiological images displayed as two-dimensional images on the monitor 9. The input unit 7 receives input of radiographing conditions or the like or input of operation instructions from a radiographer.

The monitor 9 is configured to display a stereoscopic image using two radiological image signals output from the computer 8 and to display radiological images based on the two radiological image signals as two-dimensional images. As the configuration for displaying a stereoscopic image, for example, a configuration for displaying a stereoscopic image by displaying radiological images based on two radiological image signals on two screens, respectively, and causing one radiological image to be incident on the right eye of an observer and the other radiological image to be incident on the left eye of the observer through the use of a half mirror, a polarization glass, or the like can be employed. Alternatively, for example, a configuration for creating a stereoscopic image by displaying two radiological images to overlap with each other with a predetermined amount of parallax and observing the displayed radiological images with a polarization glass or a configuration for creating a stereoscopic image by displaying two radiological images on a 3D liquid crystal panel which can be stereoscopically viewed like a parallax barrier type or a lenticular type may be employed. The unit displaying a stereoscopic image and the unit displaying two-dimensional images may be constructed as separate constituents, or may be constructed as the same unit when they can be displayed on the same screen.

Figure 5:
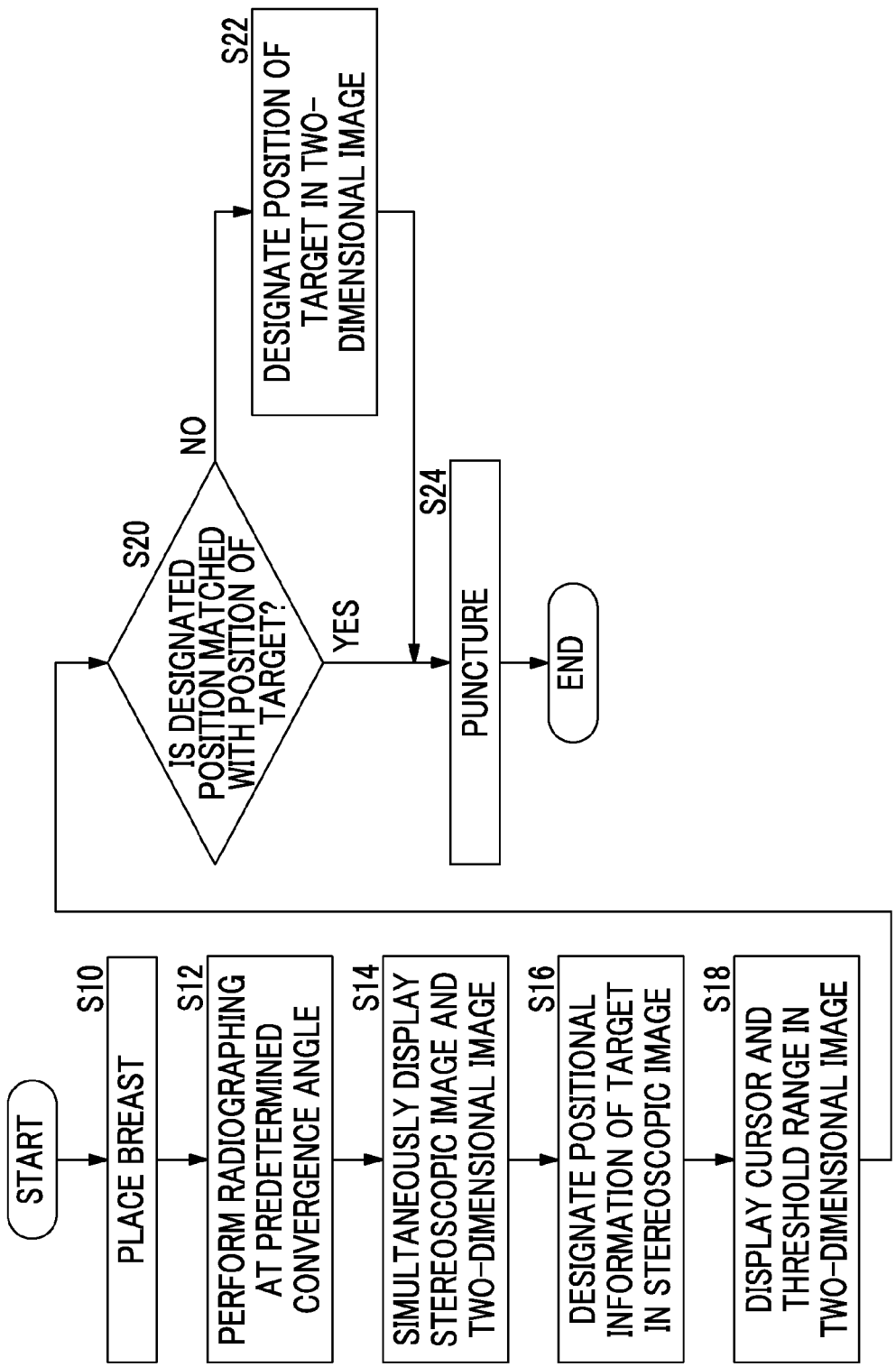
FIG. 5 is a flowchart illustrating the operation of the stereoscopic breast image radiographing and displaying system employing an embodiment of a radiological image radiographing and displaying system according to the present invention.

The operation of the breast image radiographing and displaying system according to this embodiment will be described below with reference to the flowchart shown in FIG. 5.

First, a breast M is placed on the radiography platform 14 and the breast is compressed by the compression plate 18 with a predetermined pressure (S10).

Then, through the use of the input unit 7, various radiographing conditions are input and then an instruction to start the radiographing is input by a radiographer. At this time, it is assumed that the biopsy needle unit 22 retracted to the upside and does not pierce the breast yet.

When an instruction to start the radiographing is given from the input unit 7, the stereoscopic image of the breast M is captured (S12). Specifically, first, the control unit 8a reads a predetermined convergence angle θ for radiographing a stereoscopic image and outputs information of the read convergence angle θ to the arm controller 31. In this embodiment, it is assumed that θ=±2° is stored in advance as the information of the convergence angle θ, but the present invention is not limited to this assumption and any angle may be used, for example, as long as it is in a range of ±2° to ±5°.

The information of the convergence angle θ output from the control unit 8a is received by the arm controller 31, and the arm controller 31 outputs a control signal on the basis of the information of the convergence angle θ so that the arm unit 13 rotates by +θ° about the direction perpendicular to the radiography platform 14 as shown in FIG. 2. That is, in this embodiment, a control signal is output to cause the arm unit 13 to rotate by +2° about the direction perpendicular to the radiography platform 14.

The arm unit 13 rotates by +2° in accordance with the control signal output from the arm controller 31. Subsequently, the control unit 8a outputs a control signal to the source controller 32 and the detector controller 33 so as to perform irradiation with radiation and reading of a radiological image signal. In accordance with the control signal, radiation is emitted from the radiation source 17, a radiological image obtained by radiographing the breast from the direction of +2° is detected by the radiological image detector 15, the radiological image signal is read by the detector controller 33, the radiological image signal is subjected to a predetermined signal process, and the resultant signal is stored in the radiological image storage unit 8b of the computer 8.

Then, the arm controller 31 temporarily returns the arm unit to the initial position as shown in FIG. 2, and then outputs a control signal so as to cause the arm unit to rotate by −θ° about the direction perpendicular to the radiography platform 14. That is, in this embodiment, a control signal is output so as to cause the arm unit 13 to rotate by −2° about the direction perpendicular to the radiography platform 14.

The arm unit 13 rotates by −2° in accordance with the control signal output from the arm controller 31. Subsequently, the control unit 8a outputs a control signal to the source controller 32 and the detector controller 33 so as to perform irradiation with radiation and reading of a radiological image signal. In accordance with the control signal, radiation is emitted from the radiation source 17, a radiological image obtained by radiographing the breast from the direction of −2° is detected by the radiological image detector 15, the radiological image signal is read by the detector controller 33, the radiological image signal is subjected to a predetermined signal process, and the resultant signal is stored in the radiological image storage unit 8b of the computer 8.

Figure 6:
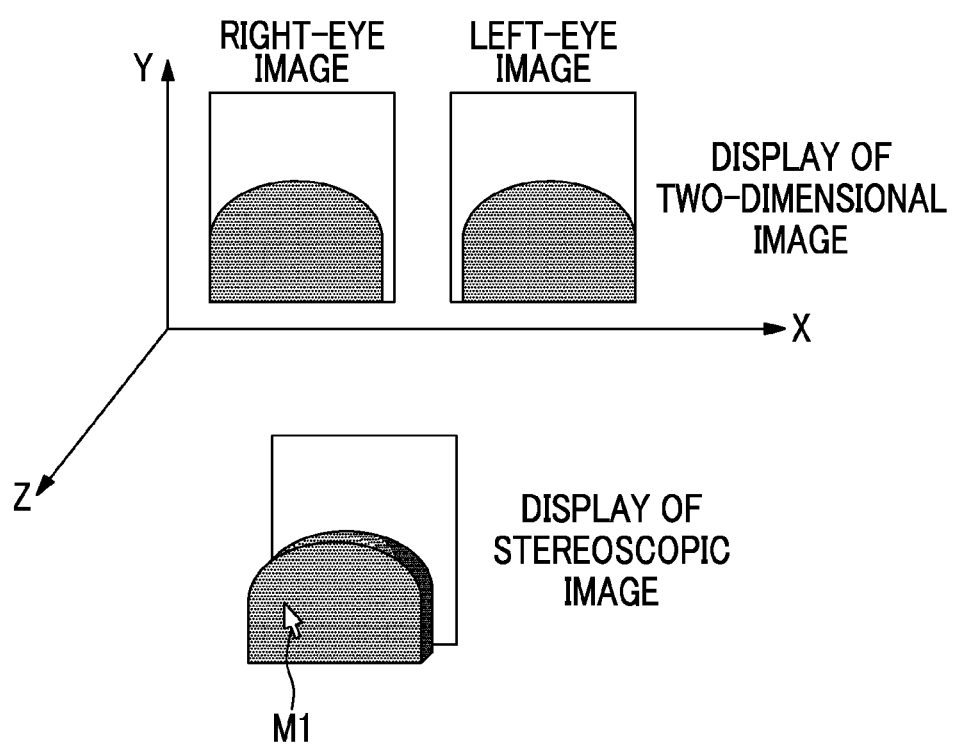
FIG. 6 is a diagram schematically illustrating an example of a stereoscopic image and two-dimensional images displayed on a monitor.

Two radiological image signals stored in the radiological image storage unit 8b of the computer 8 are read from the radiological image storage unit 8b, are then subjected to a predetermined signal process, and are then output to the monitor 9. In the monitor 9 of this embodiment, a stereoscopic image is displayed on the basis of the two radiological image signals, and radiological images as two-dimensional images are displayed on the radiological image signals at the same time as displaying the stereoscopic image (S14). FIG. 6 is a diagram schematically illustrating the display of a stereoscopic image and the display of two-dimensional images.

Then, when a calcified portion, a tumor mass, or the like in the breast is found by an observer and it is intended to collect such tissue fragments by the use of the biopsy unit 2, or the like, after the stereoscopic image and the two-dimensional images of the breast are displayed as described above, a target such as the calcified portion or the tumor mass is designated in the stereoscopic image displayed on the monitor 9 by the observer (S16).

The designation of a target can be performed, for example, by the use of a pointing device such as a mouse in the input unit 7. Specifically, a target can be designated, for example, by displaying a three-dimensional cursor mark in each of the two radiological images constituting the stereoscopic image and causing a three-dimensional cursor (M1 in FIG. 6) which is a stereoscopic image constructed by the two marks to move through the use of the input unit 7. It is assumed that the coordinate position is set on the basis of the radiographing direction in which the stereoscopic image is radiographed so that positions of the marks in the radiological images indicate the same position.

Figure 7:
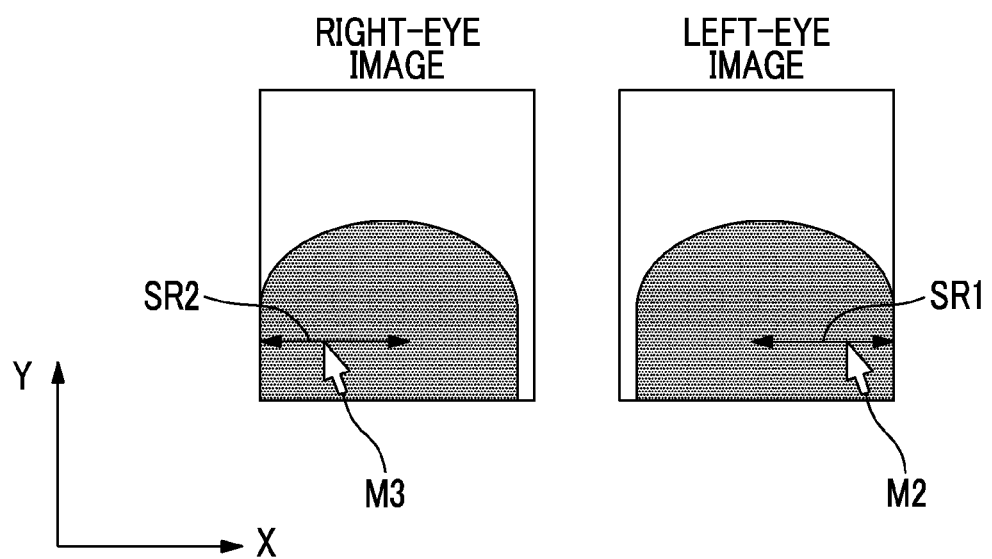
FIG. 7 is a diagram illustrating an example of a cursor and a threshold range displayed in the two-dimensional images.

The position information (x1, y1, z1) of the target designated by the observer is acquired by the control unit 8a, and the control unit 8a acquires the position information (x2, y2) and (x3, y3) in the two-dimensional images corresponding to the acquired position information (x1, y1, z1) and displays the cursor M2 and the cursor M3 as shown in FIG. 7 on the basis of the position information (x2, y2) and (x3, y3) (S18). In this embodiment, since the moving direction of the radiation source 17 is the X direction, it is assumed that y1=y2=y3 is established in the y coordinates but the x coordinates are calculated on the basis of x1, z1, and the radiographing directions of the radiological images. Specifically, the calculation is performed, for example, using trigonometry.

In this embodiment, a threshold range SR1 and a threshold range SR2 are displayed in the two-dimensional images, respectively, along with the above-mentioned cursors M2 and M3. The threshold range SR1 and the threshold range SR2 are calculated on the basis of a predetermined threshold value in the Z direction and the radiographing directions of the radiological images.

Figure 8:
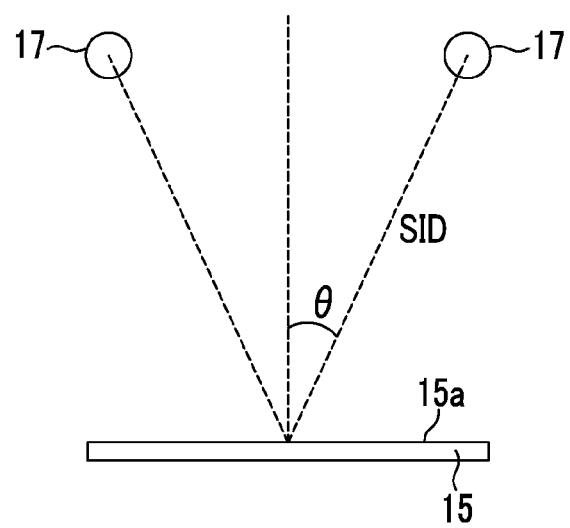
FIG. 8 is a diagram illustrating a method of calculating a threshold range SR1 and a threshold range SR2 displayed in two-dimensional images.

Specifically, for example, by substituting the threshold value ΔZR in the Z direction for Expression 1, the threshold range ΔXR(SR1, SR2) in the X direction can be calculated. As shown in FIG. 8, SID in Expression 1 represents the distance between the radiation source 17 and the detection plane 15a of the radiological image detector 15 in the optical axis direction of radiation, and θ represents the angle formed by the optical axis direction of radiation and the direction perpendicular to the detection plane 15a.

$$\Delta XR = (SID \times \sin\theta \times \Delta ZR)/(SID \times \cos\theta - \Delta ZR) \qquad (1)$$

The threshold value in the Z direction can employ, for example, the compression thickness of a breast, but other values may be employed as long as they can be used as a mark of the range in the Z direction. For example, a numerical value such as ±1 mm may be substituted.

The threshold value ΔZR may be determined depending on a resolution in the Z direction, that is, in the depth direction, determined by the distance between the focal point of the radiation source 17 and the radiological image detector 15 and the convergence angle formed by the radiographing directions of two radiological images. Specifically, since the resolution ΔZ in the Z direction is calculated by Expression 2, an integer multiple of the resolution ΔZ can be preferably set as the threshold value ΔZR.

$$\Delta Z = (SID \times \cos\theta \times \Delta x)/(SID \times \sin\theta + \Delta x) \quad (2)$$

SID and θ in Expression 2 are the same as in Expression 1, and Δx represents the resolution of the radiological image detector 15 in the X direction.

By displaying the threshold ranges SR1 and SR2 set in this way, it is possible to narrow the observation range of the observer and thus to more easily designate a target.

Although the purpose is different from that of the above-mentioned designation of a target, the range of a suction opening extending in the Z direction in the tip of the biopsy needle 21 may be displayed in the two-dimensional images or the stereoscopic image. The length of the suction opening is set in advance, and the preset length may be substituted for ΔZR of Expression 1 to calculate ΔXR and the range of ΔXR may be displayed as the range of the opening in the two-dimensional images, when the length of the suction opening is displayed in the two-dimensional images. When the length of the suction opening is displayed in the stereoscopic image, the range of ΔXR may be displayed as the range of the opening in the two-dimensional radiological images constituting the stereoscopic image. By displaying the range of the opening in this way, it is possible to recognize the suction range.

Then, within the threshold range SR1 and the threshold range SR2 in the two-dimensional images, it is determined by the observer whether the position of the target such as an actual abnormal shadow is matched with the positions of the cursors M2 and M3 (S20).

Here, when it is determined by the observer that the position of the target is not matched with the positions of the cursors M2 and M3, the observer operates the cursor M2 and the cursor M3 through the use of the input unit 7 so that the position of the target is matched with the positions of the cursors M2 and M3, whereby the position of the target is designated again by the use of the cursor M2 and the cursor M3 (S22).

the position information (x1', y1', z1') of the target in the stereoscopic image is calculated again by the control unit 8a on the basis of the position information (x2', y2') of the cursor M2 and the position information (x3', y3') of the cursor M3 designated again in the two-dimensional images by the observer.

The control unit 8a outputs the calculated position information (x1', y1', z1') to the needle position controller 35 of the biopsy unit 2.

In this state, when a predetermined operation button in the input unit 7 is pressed, a control signal for moving the biopsy needle 21 is output from the control unit 8a to the needle position controller 35. The needle position controller 35 causes the biopsy needle 21 so as to locate the tip of the biopsy needle 21 at the position indicated by the coordinate (x1', y1', z1'+α) on the basis of the previously-input value of the position information (x1', y1', z1'). Here, α is set to a large value enough to cause the biopsy needle 21 not to pierce the breast. As a result, the biopsy needle 21 is set to the upside of the target.

Thereafter, when the observer performs a predetermined operation for instructing to insert the biopsy needle 21 through the use of the input unit 7, the biopsy needle 21 moves so as to locate the tip of the biopsy needle 21 at the position indicated by the coordinate (x1', y1', z1') under the control of the control unit 8a and the needle position controller 35, and the breast is punctured by the biopsy needle 21 (S24).

On the other hand, in S20, when it is determined by the observer that the position of the target is matched with the positions 13 of the cursors M2 and M3, the observer presses a predetermined operation button through the use of the input unit 7 and the control unit 8a outputs the position information (x1, y1, and z1) designated in the stereoscopic image by the observer to the needle position controller 35 of the biopsy unit 2.

In this state, when a predetermined operation button in the input unit 7 is pressed, a control signal for causing the biopsy needle 21 to move is output from the control unit 8a to the needle position controller 35. The needle position controller 35 causes the biopsy needle 21 so as to locate the tip of the biopsy needle 21 at the position indicated by the coordinate (x1, y1, z1+α) on the basis of the previously-input value of the position information (x1, y1, z1).

Thereafter, when the observer performs a predetermined operation for instructing to insert the biopsy needle 21 through the use of the input unit 7, the biopsy needle 21 moves so as to locate the tip of the biopsy needle 21 at the position indicated by the coordinate (x1, y1, z1) under the control of the control unit 8a and the needle position controller 35, and the breast is punctured by the biopsy needle 21 (S24).

In the description of this embodiment, radiological image signals acquired at the same convergence angle $\pm\theta = \pm 2°$ are used as the radiological image signals for displaying the stereoscopic image and the radiological image signals for displaying the two-dimensional images, but the present invention is not limited to this. The two-dimensional images may be displayed using the radiological image signals acquired at a convergence angle different from the convergence angle when acquiring the radiological image signals for displaying the stereoscopic image. Specifically, the convergence angle for acquiring the radiological image signals for displaying two-dimensional images is preferably set to be larger. For example, the convergence angle is preferably in a range of 10° (±5°) to 30° (±15°). By setting the convergence angle to be larger in this way, the amount of shift in the depth direction of the radiological image signal can be made to increase, whereby it is possible to enhance the position resolution and to designate a specific position in a subject with high accuracy.

When the convergence angle is set as described above, the stereoscopic image and the two-dimensional images may not be simultaneously displayed. For example, first, the radiographing is performed at the convergence angle of $\pm\theta = \pm 2°$, only the stereoscopic image is displayed on the basis of the radiological image signals acquired through the radiographing, and the designation of a target in the stereoscopic image is received as described above.

Then, the radiographing is performed again at a convergence angle of $\pm\theta' = \pm 15°$, and the two-dimensional images are displayed on the basis of the radiological image signals acquired through the radiographing. In the same way as described above, the cursors M2 and M3 are displayed at the positions in the two-dimensional images corresponding to the position of the target designated in the stereoscopic image, the threshold ranges SR1 and SR2 are displayed therein, and it can be determined by the observer whether the actual position of the target and the positions of the cursors M2 and M3 are matched with each other in the threshold ranges SR1 and SR2. The subsequent processes are the same as described in the above-mentioned embodiment.

Figure 9:
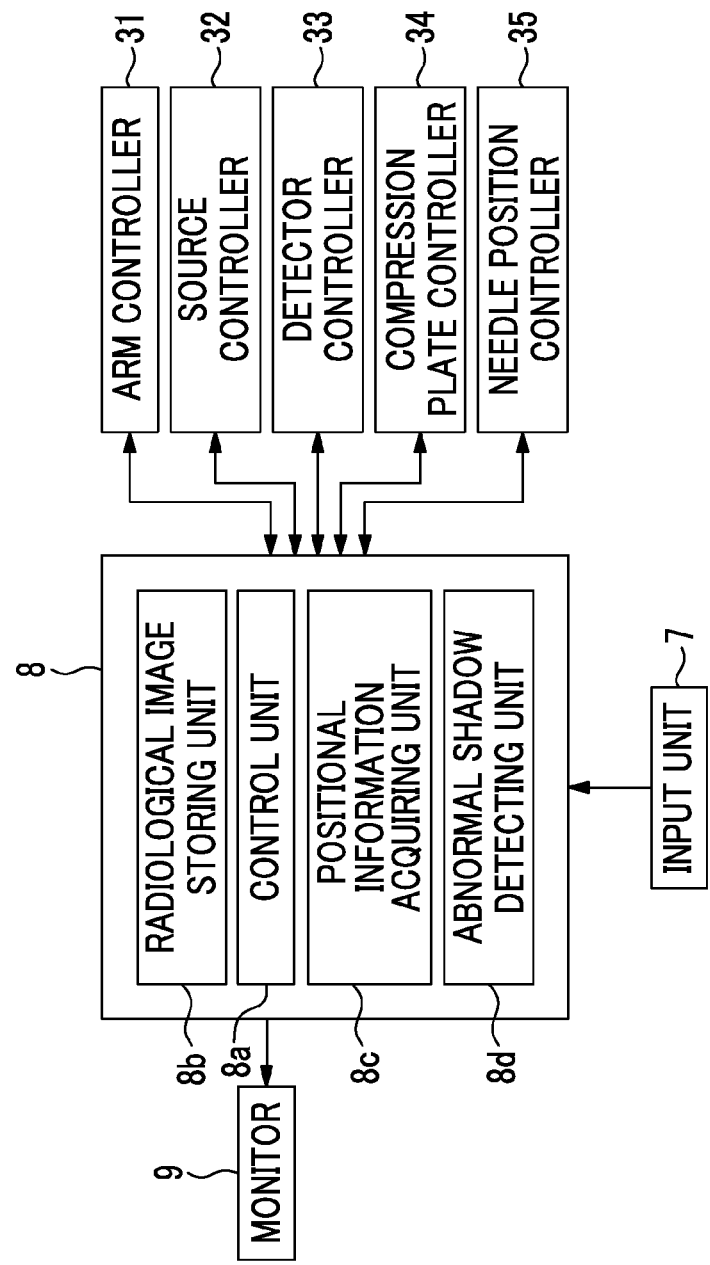
FIG. 9 is a block diagram illustrating a stereoscopic breast image radiographing and displaying system employing another embodiment of the radiological image radiographing and displaying system according to the present invention.

As shown in FIG. 9, the stereoscopic breast image radiographing and displaying system according to the above-mentioned embodiment may further include an abnormal shadow detecting unit 8*d*. In this case, the abnormal shadow detecting unit 8*d* may automatically detect the position of the abnormal shadow in the breast and the monitor 9 may display a mark representing the position of the abnormal shadow. The abnormal shadow may be detected on the basis of features in concentration distribution or features in shape of the abnormal shadow. Specifically, the abnormal shadow can be detected using an iris filter process suitable mainly for detecting a tumor mass shadow, a morphology filter process suitable mainly for detecting a fine calcified shadow, or the like.

Figure 10:
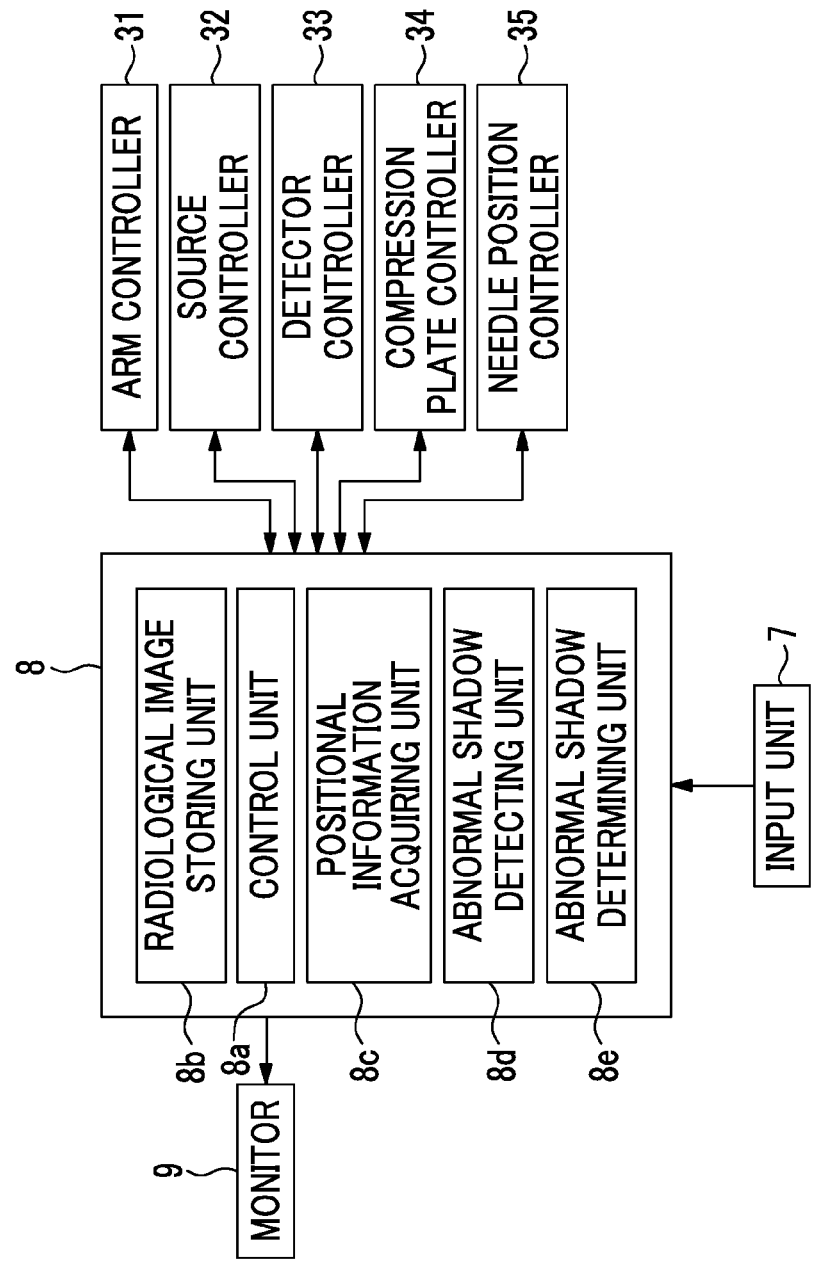
FIG. 10 is a block diagram illustrating a stereoscopic breast image radiographing and displaying system employing another embodiment of the radiological image radiographing and displaying system according to the present invention.

It may be further determined whether an abnormal shadow exists in the needle insertion path of the biopsy needle 21 on the basis of the position information of the abnormal shadow detected by the abnormal shadow detecting unit 8*d* and the position information of the target finally determined, that is, the position coordinate (x1, y1, z1) of the position which the tip of the biopsy needle 21 reaches. Specifically, as shown in FIG. 10, an abnormal shadow determining unit 8*e* may be further provided and the abnormal shadow determination unit 8*e* may determine whether an abnormal shadow exists in a straight line extending upward in the Z direction from the position coordinate (x1, y1, z1) at which the tip of the biopsy needle 21 reaches as a start point. When the abnormal shadow determination unit 8*e* determines that an abnormal shadow exists in the needle insertion path of the biopsy needle 21, the intent can be notified by displaying the intent on the monitor 9 or the like so as to stop the needling. Alternatively, the control unit 8*a* may perform a control operation of performing the needling when the abnormal shadow determination unit 8*e* determines that an abnormal shadow does not exist in the needle insertion path of the biopsy needle 21 and not performing the needling when it is determined that an abnormal shadow exists in the needle insertion path. Accordingly, it is possible to prevent the biopsy needle 21 from passing through the abnormal shadow to metastasize to the other normal sites.

Although it is stated above that it is determined whether an abnormal shadow exists in the needle insertion path of the biopsy needle 21 using the position information of the abnormal shadow detected by the abnormal shadow detecting unit 8*d*, the automatic detection of an abnormal shadow may not be performed necessarily. For example, a straight line extending upward in the Z direction from the position coordinate (x1, y1, z1) which the tip of the biopsy needle 21 reaches as a start point may be displayed as a needle insertion path in the stereoscopic image or the two-dimensional images on the monitor 9 and the observer may be allowed to determine whether an abnormal shadow exists in the displayed needle insertion path.

Although it is stated above that the straight line extending upward in the Z direction from the position coordinate which the tip of the biopsy needle 21 reaches as a start point is used as the needle insertion path, the present invention is not limited to this. For example, designation of at least a point in a desired needle insertion path may be received by the input unit 7 and the needle insertion path may be estimated on the basis of the received point and the position coordinate which the tip of the biopsy needle 21 reaches. In the estimation of the needle insertion path, for example, the designated point and the position coordinate which the tip of the biopsy needle 21 reaches may be connected to each other with a straight line, or a curve pattern may be stored in advance and the designated point and the position coordinate which the tip of the biopsy needle 21 reaches may be connected with the curve pattern. The selection of the straight line or the curve connecting the designated point and the position coordinate which the tip of the biopsy needle 21 reaches may be received through the use of the input unit 7. When the needle insertion path is estimated in this way, the biopsy needle 21 may be controlled to move along the estimated needle insertion path.

Although it is stated above that the needle insertion path is displayed as a straight line, the present invention is not limited to this. For example, in general radiographing systems other than the breast image radiographing system, it may be intended to insert the biopsy needle so as to avoid the ribs. In this case, a curved biopsy needle is used instead of a straight shape. Therefore, in this case, the needle insertion path may be displayed as a curve corresponding to the shape of the biopsy needle, instead of the straight shape. Regarding the display of the needle insertion path, the shape of the biopsy needle itself may be displayed as the needle insertion path in the stereoscopic image or the two-dimensional images to overlap with each other, or a needle insertion path may be calculated on the basis of the position coordinate which the tip of the biopsy needle 21 reaches and the shape of the biopsy needle and the calculated needle insertion path may be displayed. Regarding the shape information of the biopsy needle, the shape information corresponding to plural biopsy needles may be set in advance and one thereof may be selected by the observer.

In the stereoscopic breast image radiographing and displaying system according to the above-mentioned embodiment, the stereoscopic image and the two-dimensional images are simultaneously displayed, but the present invention is not limited to this. The stereoscopic image and the two-dimensional images may be switched and displayed in accordance with an instruction from the input unit 7.

Although it is stated above that an embodiment of the radiological image radiographing and displaying system according to the present invention is applied to the stereoscopic breast image radiographing and displaying system, the subject in the present invention is not limited to the breast, but the present invention can be applied, for example, to radiological image radiographing and displaying systems for radiographing the chest, the head, and the like.

What is claimed is:

1. A radiological image radiographing and displaying system having a radiation emitting unit that irradiates a subject with radiation from different radiographing directions, a radiological image detector that detects the radiation emitted from the radiation emitting unit and passing through the subject, and a display unit that acquires radiological images radiographed in each radiographing direction which is detected by the radiological image detector and that displays a stereoscopic image using the acquired radiological images of the radiographing directions, the system comprising:

an input device configured to designate, according to user input, a three-dimensional position in the stereoscopic image when the stereoscopic image is displayed on the display unit; and a computing device configured to acquire three-dimensional position information based on the designation of the three-dimensional position by the input device, wherein the display unit is configured to display the stereoscopic image as a three-dimensional image and each radiological image radiographed in each radiographing direction as two-dimensional images and is configured to display a mark based on the three-dimensional position information acquired by the computing device in each of the two-dimensional images, and wherein the input device is further configured to move the mark according to user input to designate a two-dimensional position in each of the two-dimensional images after the mark is displayed in each of the two-dimensional images, wherein the computing device is further configured to acquire other three-dimensional position information based on the designation of the two-dimensional position by the input device in the case that the input device has designated the two-dimensional position in at least one of the two-dimensional images, such that the three-dimensional position in the stereoscopic image is changed based on the other position information, wherein the display unit includes a monitor and is further configured to display an image on the monitor, the image representing a predetermined threshold range in the two-dimensional images on the basis of coordinates in the depth direction of the position designated in the stereoscopic image, wherein the computing device is configured to calculate the predetermined threshold range, wherein the computing device is configured to calculate the predetermined threshold range depending on a resolution in the depth direction determined on the basis of the distance between the focal point of radiation of the radiation emitting unit and the radiological image detector and a convergence angle formed by the radiographing directions.

2. The radiological image radiographing and displaying system according to claim 1, wherein the display unit includes a monitor and is further configured to display the stereoscopic image and the two-dimensional images simultaneously on the monitor.

3. The radiological image radiographing and displaying system according to claim 1, wherein the radiological images displayed as the two-dimensional images are acquired through irradiation with radiation from radiographing directions which form a convergence angle larger than the convergence angle formed by the radiographing directions of the radiological images constituting the stereoscopic image used to receive the designation of the position by the input device.

4. The radiological image radiographing and displaying system according to claim 2, wherein the radiological images displayed as the two-dimensional images are acquired through irradiation with radiation from radiographing directions which form a convergence angle larger than the convergence angle formed by the radiographing directions of the radiological images constituting the stereoscopic image used to receive the designation of the position by the input device.

5. The radiological image radiographing and displaying system according to claim 1, wherein the radiological images displayed as the two-dimensional images are acquired through irradiation with radiation from radiographing directions which form a convergence angle larger than the convergence angle formed by the radiographing directions of the radiological images constituting the stereoscopic image used to receive the designation of the position by the input device.

6. The radiological image radiographing and displaying system according to claim 1, wherein the computing device is further configured to detect an abnormal shadow in the two-dimensional images.

7. The radiological image radiographing and displaying system according to claim 2, wherein the computing device is further configured to detect an abnormal shadow in the two-dimensional images.

8. The radiological image radiographing and displaying system according to claim 1, wherein the computing device is further configured to detect an abnormal shadow in the two-dimensional images.

9. The radiological image radiographing and displaying system according to claim 6, wherein the display unit displays another mark representing the position of the abnormal shadow detected by the computing device in the two-dimensional images.

10. The radiological image radiographing and displaying system according to claim 6, further comprising:
    a needle supporting unit that supports a biopsy needle and that is movable on the basis of the position designated in the stereoscopic image or the position designated in the two-dimensional images;
    wherein the computing device is further configured to determine whether the abnormal shadow exists in a needle insertion path of the biopsy needle estimated on the basis of the position designated in the stereoscopic image or the position designated in the two-dimensional images.

11. The radiological image radiographing and displaying system according to claim 9, further comprising:
    a needle supporting unit that supports a biopsy needle and that is movable on the basis of the position designated in the stereoscopic image or the position designated in the two-dimensional images;
    wherein the computing device is further configured to determine whether the abnormal shadow exists in a needle insertion path of the biopsy needle estimated on the basis of the position designated in the stereoscopic image or the position designated in the two-dimensional images.

12. The radiological image radiographing and displaying system according to claim 10, wherein the input device is further configured to designate at least one point in a desired needle insertion path of the biopsy needle,
    wherein the computing device is further configured to determine whether the abnormal shadow exists in the needle insertion path which is estimated on the basis of the position designated in the stereoscopic image or the position designated in the two-dimensional images and the point received by the input device.

13. The radiological image radiographing and displaying system according to claim 11, wherein the input device is further configured to designate at least one point in a desired needle insertion path of the biopsy needle,
    wherein the computing device is further configured to determine whether the abnormal shadow exists in the needle insertion path which is estimated on the basis of the position designated in the stereoscopic image or the position designated in the two-dimensional images and the point received by the input device.

14. The radiological image radiographing and displaying system according to claim 10, wherein the biopsy needle moves along the estimated needle insertion path of the biopsy needle in the case that the computing device has determined that the abnormal shadow does not exist.

15. The radiological image radiographing and displaying system according to claim 12, wherein the biopsy needle moves along the estimated needle insertion path of the biopsy needle in the case that the computing device has determined that the abnormal shadow does not exist.

16. A mammography system having a radiography platform, a compression paddle, a radiation emitting unit that irradiates a breast with radiation from different radiographing directions while the breast is compressed between the radiography platform and the compression paddle, a radiological image detector that is located inside the radiography platform and detects the radiation emitted from the radiation emitting unit and passing through the breast, and a display unit that acquires radiological images radiographed in each radiographing direction which is detected by the radiological image detector and that displays a stereoscopic image using the acquired radiological images of the radiographing directions, the system comprising:

an input device configured to designate, according to user input, a three-dimensional position in the stereoscopic image when the stereoscopic image is displayed on the display unit; and a computing device configured to acquire three-dimensional position information based on the designation of the three-dimensional position by the input device, wherein the display unit is configured to display the stereoscopic image as a three-dimensional image and each radiological image radiographed in each radiographing direction as two-dimensional images and is configured to display a mark based on the three-dimensional position information acquired by the computing device in each of the two-dimensional images, and wherein the input device is further configured to move the mark according to user input to designate a two-dimensional position in each of the two-dimensional images after the mark is displayed in each of the two-dimensional images, wherein the computing device is further configured to acquire other three-dimensional position information based on the designation of the two-dimensional position by the input device in the case that the input device has designated the two-dimensional position in at least one of the two-dimensional images, such that the three-dimensional position in the stereoscopic image is changed based on the other position information, wherein the display unit includes a monitor and is further configured to display an image on the monitor, the image representing a predetermined threshold range in the two-dimensional images on the basis of coordinates in the depth direction of the position designated in the stereoscopic image, wherein the computing device is configured to calculate the predetermined threshold range, wherein the computing device is configured to calculate the predetermined threshold range depending on a resolution in the depth direction determined on the basis of the distance between the focal point of radiation of the radiation emitting unit and the radiological image detector and a convergence angle formed by the radiographing directions.

* * * * *